United States Patent
Daniel et al.

(10) Patent No.: US 10,709,561 B2
(45) Date of Patent: Jul. 14, 2020

(54) EXTERNALLY FED GRAFT CONTAINMENT CAGE/SCAFFOLD

(71) Applicant: DePuy Synthes Products, Inc., Raynham, MA (US)

(72) Inventors: Steffan Daniel, Zuchwil (CH); André Furrer, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 13 days.

(21) Appl. No.: 16/022,123

(22) Filed: Jun. 28, 2018

(65) Prior Publication Data

US 2019/0076253 A1 Mar. 14, 2019

Related U.S. Application Data

(60) Provisional application No. 62/557,521, filed on Sep. 12, 2017.

(51) Int. Cl.
| | | |
|---|---|---|
| *A61F 2/28* | (2006.01) | |
| *A61B 17/88* | (2006.01) | |
| *A61L 27/36* | (2006.01) | |
| *A61F 2/30* | (2006.01) | |

(52) U.S. Cl.
CPC .......... *A61F 2/2846* (2013.01); *A61F 2/2803* (2013.01); *A61B 17/8805* (2013.01); *A61F 2002/2817* (2013.01); *A61F 2002/2835* (2013.01); *A61F 2002/30578* (2013.01); *A61F 2002/30914* (2013.01); *A61L 27/3608* (2013.01)

(58) Field of Classification Search
CPC .... A61F 2/2846; A61F 2/2803; A61F 2/4601; A61F 2/2835; A61F 2/4455; A61B 17/8805; A61B 17/7097; A61B 17/8833; A61B 17/3472; A61B 17/8802; A61B 17/8816; A61B 17/7061
See application file for complete search history.

(56) References Cited

U.S. PATENT DOCUMENTS

| | | | | |
|---|---|---|---|---|
| 5,211,664 | A * | 5/1993 | Tepic | A61F 2/2846 606/60 |
| 9,561,354 | B2 * | 2/2017 | Nebosky | A61B 17/56 |
| 10,022,233 | B1 * | 7/2018 | Gall | A61F 2/30771 |
| 2012/0296441 | A1 * | 11/2012 | Mikhail | A61F 2/2803 623/23.63 |

(Continued)

*Primary Examiner* — Marcia L Watkins
(74) *Attorney, Agent, or Firm* — Fay Kaplun & Marcin, LLP

(57) ABSTRACT

A bone graft containment device includes a body extending longitudinally from a first end to a second end. The body includes a channel extending longitudinally therethrough. The device also includes a fluid delivery structure received within the channel. The fluid delivery structure includes a central tubular member extending along a length of the channel and a laterally extending tubular member extending laterally from the central tubular member to a fluid receiving opening. The central tubular member includes a plurality of openings extending laterally through a wall thereof, so that, when the fluid receiving opening is connected to an external fluid source, fluid is passed through the laterally extending tubular member and the central tubular member to be dispersed to a graft material packed within the channel via the plurality of openings.

16 Claims, 2 Drawing Sheets

(56) References Cited

U.S. PATENT DOCUMENTS

| | | | |
|---|---|---|---|
| 2013/0338775 A1* | 12/2013 | Biedermann | A61F 2/44 623/17.16 |
| 2014/0039565 A1* | 2/2014 | Martineau | A61B 17/8625 606/304 |
| 2018/0193530 A1 | 7/2018 | Barbas et al. | |

* cited by examiner

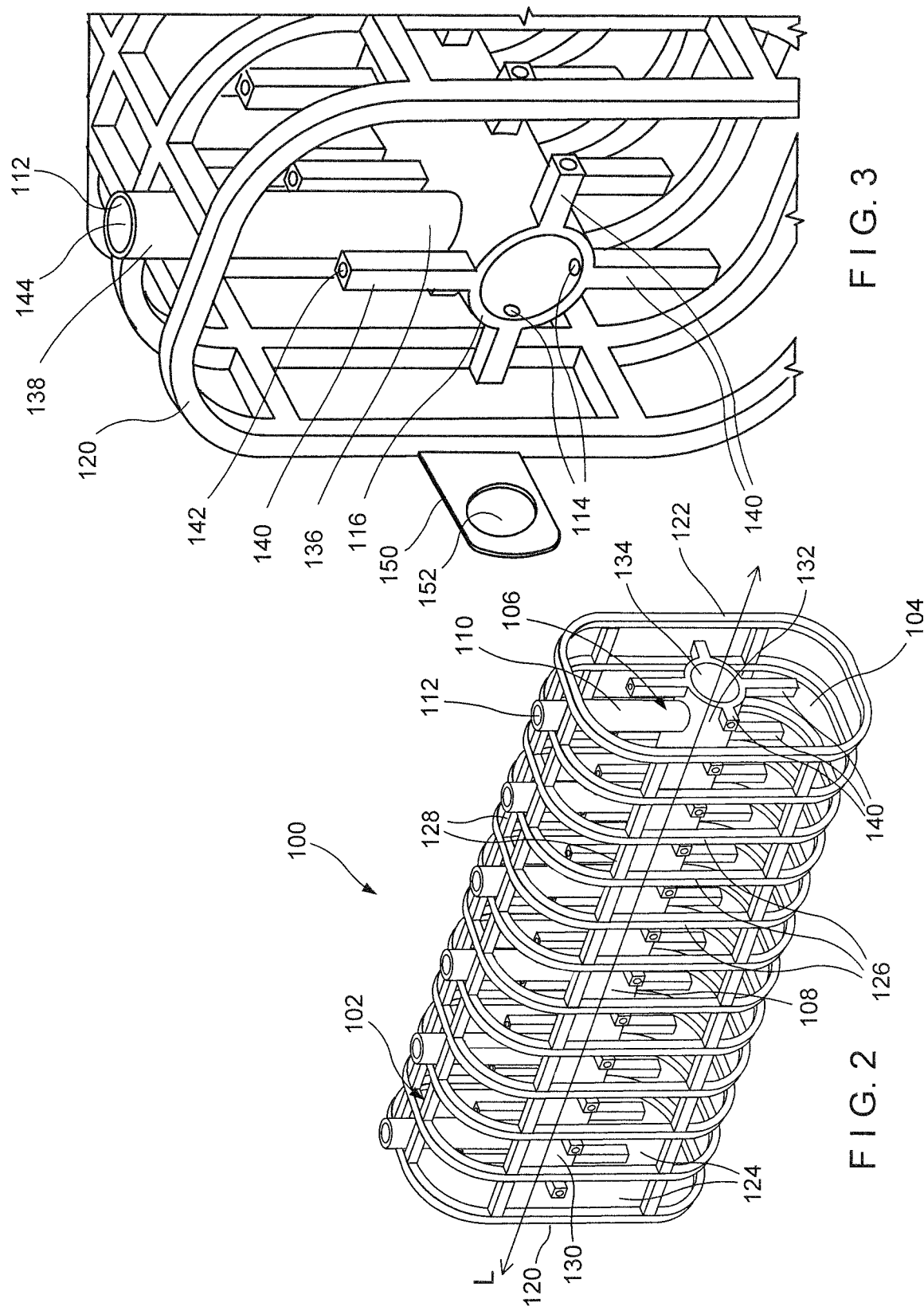

EXTERNALLY FED GRAFT CONTAINMENT CAGE/SCAFFOLD

PRIORITY CLAIM

The present application claims priority to U.S. Provisional Patent Application Ser. No. 62/557,521 filed on Sep. 12, 2017. The specification of the above-identified application is expressly incorporated herein by reference.

BACKGROUND

Mandible defects are often treated with bone grafts and/or implants such as, bone plates, to assist with healing. The bone grafts may be placed in the target area using any of a variety of methods. However, without a container for the bone graft, the graft may fall away from a target site before it can be incorporated by the body into the healing bone.

SUMMARY

The present embodiments are directed to a bone graft containment device, comprising a body extending longitudinally from a first end to a second end and including a channel extending longitudinally therethrough and a fluid delivery structure received within the channel, the fluid delivery structure including a central tubular member extending along a length of the channel and a laterally extending tubular member extending laterally from the central tubular member to a fluid receiving opening, the central tubular member including a plurality of openings extending laterally through a wall thereof, so that, when the fluid receiving opening is connected to an external fluid source, fluid is passed through the laterally extending tubular member and the central tubular member to be dispersed to a graft material packed within the channel via the plurality of openings.

The present embodiments are also directed to a system for treating a bone, comprising a mesh graft containment device extending longitudinally from a first end to a second end, a fluid delivery structure received within a channel of the mesh graft containment device, the fluid delivery structure including a central tubular member extending along a length of the channel and a laterally extending tubular member extending laterally from the central tubular member to a fluid receiving opening, the central tubular member including a plurality of openings extending laterally through a wall thereof and an external fluid source connectable to the fluid receiving opening of the laterally extending tubular member so that fluid is passed therethrough to the central tubular member to be dispersed to a graft material packed within the channel via the plurality of openings of the central tubular member.

The present embodiments are also directed to a method for treating a bone, comprising packing a graft material about a fluid delivery structure within a channel of a graft containment device, the graft containment device including a mesh body extending longitudinally from a first end to a second end and including the channel extending longitudinally therethrough, the fluid delivery structure including a central tubular member and a laterally extending tubular member extending laterally from the central tubular member in communication therewith, fixing the graft containment device in a target space of a bone and connecting an external fluid supply to the laterally extending tubular member to provide a fluid to the graft material packed within the graft containment device via a plurality of openings extending through a wall of the central tubular member.

BRIEF DESCRIPTION

FIG. 2 shows a perspective view of the device of FIG. 1; and

FIG. 3 shows an enlarged perspective view of FIG. 1.

DETAILED DESCRIPTION

Figure 1:
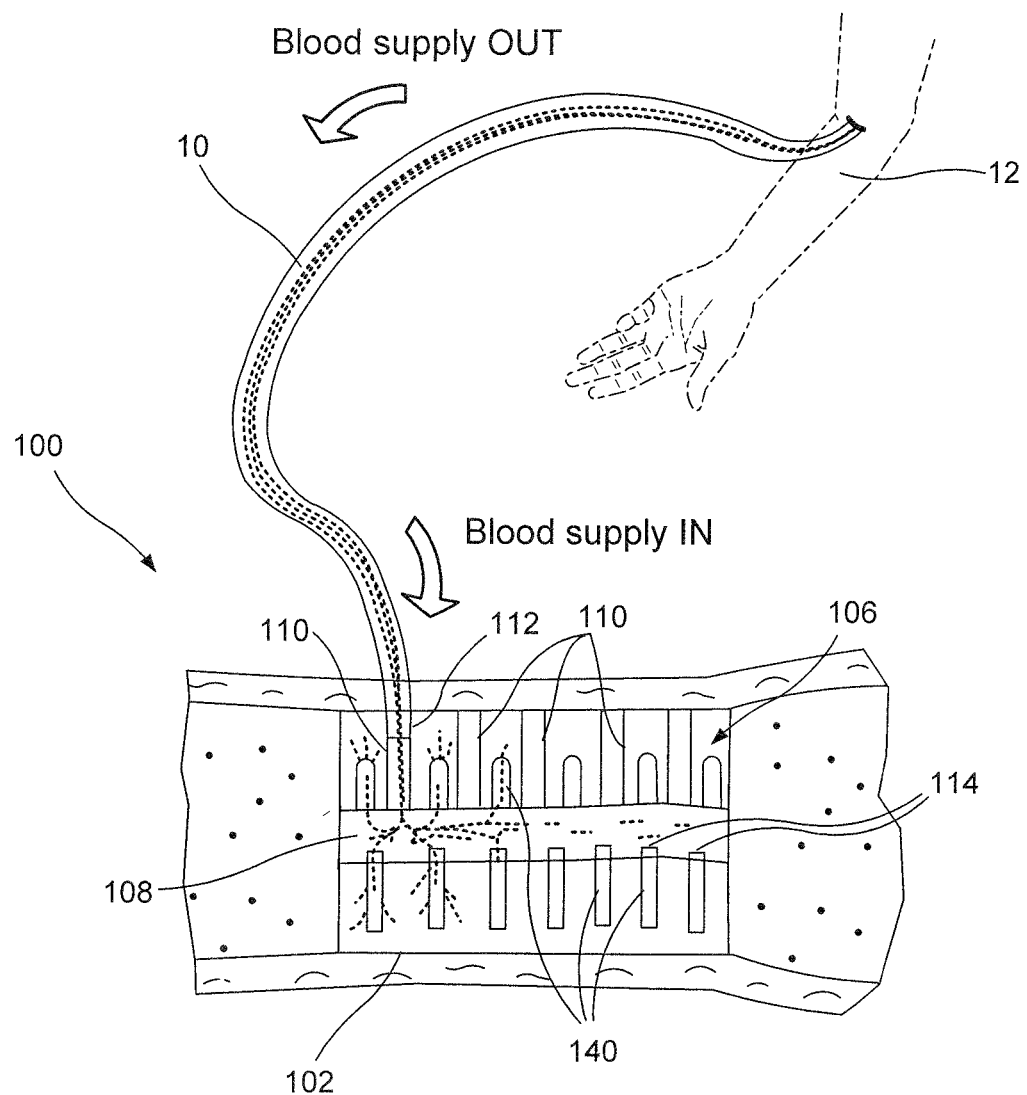
FIG. 1 shows a partially cross-sectional side view of a device according to an exemplary embodiment of the present disclosure.

The present invention may be understood with reference to the following description and the appended drawings, wherein like elements are referred to with the same reference numerals. The present invention relates to the treatment of bone and, in particular, relates to treatments using bone grafts and bone graft substitutes. Exemplary embodiments of the present invention describe a graft containment cage configured to be positioned in a gap or space in a target bone (e.g., the mandible) so that graft material may be packed therein to encourage and guide the growth of new bone into the gap/space. In one exemplary embodiment, the cage is positioned between two separated portions of bone to generate new bone joining the separated portions of bone. It will be understood by those of skill in the art, however, that the graft containment cage may be inserted or positioned within any gap or space in the target bone including, for example, at an end of the bone. Blood supply and perfusion of bone grafts is critical for the survival of cells and to encourage bone healing throughout the target area. However, in some cases, maintaining a good supply throughout the entire grafted region may be difficult. For example, particularly for larger defects, bone healing may occur at ends while a central portion of the grafted region has yet to regenerate. An exemplary embodiment of the graft containment device comprises a mesh body extending along a longitudinal axis, the mesh body defining a channel in which a graft material is to be packed. The graft containment device also includes a tubular structure extending within the channel for feeding an external blood supply to a central portion of the graft containment device to facilitate bone healing. The tubular structure includes a central tubular member extending along a length of the channel and at least one laterally extending tubular member extending laterally therefrom in communication therewith. The central tubular member includes a plurality of openings extending through a wall thereof so that, when the laterally extending tubular member is connected to an external blood supply, blood is delivered to a central portion of the graft via the openings of the central tubular member. Although the exemplary embodiment is shown and described in regard to the treatment of a mandible, it will be understood by those of skill in the art that the graft containment device of the present invention may also be formed in different shapes and sized to permit use in treating other types of bone which would benefit from the use of a graft containment device.

As shown in FIGS. 1-3, a graft containment device 100 according to an exemplary embodiment of the present disclosure extending along a longitudinal axis L and including a channel 104 extending therethrough along the longitudinal axis for receiving a graft material. Within the channel 104, the graft containment device 100 includes a delivery structure 106 for feeding an external blood supply 10 to a central portion of the graft material within the containment device 100. The delivery structure 106 includes a central tubular member 108 extending longitudinally through the channel 104 and at least one laterally extending tubular member 110 extending laterally from the central tubular member 108 and in fluid communication with the central tubular member 108. The laterally extending tubular member 110 extends from the central tubular member 108 to an opening 112 configured to be connected to the external blood supply 10 via, for example, a catheter 12 or other flexible, tubular device. The central tubular member 108 includes a plurality of openings 114 extending laterally therethrough for dispersing the blood to the graft material. In use, graft material is packed within the channel 104, around the delivery structure 106. The graft containment device 100 is then fixed in a desired position within a target gap or space of a bone (e.g., mandible). The external blood supply is connected to the laterally extending tubular member 110 to disperse blood to the graft material to encourage growth of bone in the desired position occupied by the device 100. Although the exemplary embodiment shows and describes the delivery structure 106 connected to a blood supply for dispersing blood, it will be understood by those skilled in the art that the graft containment device 100 may be similarly coupled to other sources which are also able to steadily control the delivery of fluids for delivering other fluids (e.g., medications) to the graft material.

The body 102 extends along the longitudinal axis L from a first end 120 to a second end 122 and includes the channel 104 extending therethrough along the longitudinal axis L. The body 102 includes a plurality of pores 124 extending laterally therethrough, with the pores 124 being sized to prevent graft material from falling out of the device 100 therethrough while also promoting vascularization into the device 100. In one embodiment, the body 102 is formed as a mesh of material. For example, the mesh may be formed via a lattice of circumferential and longitudinal members 126, 128, respectively, which intersect to define the pores 124. The circumferential members 126 and the longitudinal members 128 are spaced from one another by distances selected to form a desired level of porosity. In an alternate embodiment, the body 102 may be formed of a mesh material without discrete circumferential and longitudinal members 126, 128, including pores 124 sized similarly to those formed in the device 100. Some or all of the pores 124 may also be sized and shaped to receive bone fixation elements therethrough. For example, in cases in which the graft containment device 100 is used in conjunction with a fixation plate, bone fixation elements may be inserted through openings of the fixation plate and through select pores 124 of the body 102 to fix the fixation plate relative to the graft containment device 100.

As would be understood by those skilled in the art, the body 102 may be sized and shaped to correspond to the target space in the bone in which the bone graft containment device 100 is to be positioned. For example, if the body 102 is to be positioned between two separated portions of bone, a lateral cross-section of the body 102 may be selected to substantially match the shape and size of the separated portions of bone (e.g., to match a size and shape of a portion of bone which formerly occupied the space to be occupied by the device 100). Where the target bone is the mandible, the cross-section of the body 102 will be selected to substantially correspond to a cross-section of the portion of the mandible to be treated. In some cases, the body 102 may be trimmed to fit the target space. For example, a length of the body 102 may be trimmed to substantially correspond to a length of the target space to be filled. A patient-specific graft containment device 100 may be formed using, for example, 3D printing, and may be based on dimensions of the patient's specific anatomy obtained via images such as, for example, CT scans or X-rays.

The delivery structure 106 is housed within the channel 104 of the body 102. The delivery structure 106, in one embodiment, may be integrally formed with the body 102. In particular, the delivery structure 106 may be connected to the body 102 via a plurality of struts. In an alternative embodiment, the delivery structure 106 may be a separate element configured to be received within the channel 104. As described above, the delivery structure 106 includes the central tubular member 108 and at least one laterally extending tubular member 110 extending therefrom. The laterally extending tubular member 110 extends from a first end 136 connected and open to the central tubular member 108 to a second end 138 including the opening 112 configured to be connected to an external blood supply. The delivery structure 106 may be positioned within the channel 104 so that the central lumen extends longitudinally within the channel 104 while the second end 138 of the laterally extending tubular member 110 extends through one of the pores 124 of the body 102 so that the second end 138 extends beyond an exterior surface of the body 102 to be connected to the external blood supply 10.

The central tubular member 108 extends from a first end 130 to a second end 132 and includes a central lumen 134 extending therethrough. The central tubular member 108 includes a plurality of openings 114 extending through a wall 116 thereof for dispersing fluid (e.g., blood) received within the central lumen 134 to a surrounding area. In one embodiment, the delivery structure 106 may be positioned so that the central tubular member 108 extends substantially along the longitudinal axis L of the body 102. A length of the central tubular member 108 in this embodiment corresponds to a length of the body 102. It will be understood by those of skill in the art, however, that the central tubular member 108 may be positioned within the channel 104 in any of a variety of ways so long as the central tubular member 108 extends along at least a portion of a length of the body 102. For example, the central tubular member 108 may extend parallel to the longitudinal axis L or at an angle relative thereto.

In an exemplary embodiment, at least some of these openings 114 may be connected to a strut 140 extending radially outward with respect to the central tubular member 108. All or a portion of the struts 140 may include a lumen 142 extending therethrough along a length thereof and in communication with a corresponding one of the openings 114 so that the blood received within the central tubular member 108 may be dispersed deeper into the graft material surrounding the central tubular member 108. A length of the struts 140 may be selected to correspond to a desired dispersion area for the blood within the graft material. Each of the struts 140 may have varying lengths depending on a distance between an exterior of the central tubular member 108 and an interior of the body 102 and/or a desired dispersion of the blood. For example, a length of the strut 140 may be selected to extend halfway between the exterior of the central tubular member 108 and the interior of the body 102.

The laterally extending tubular member 110 extends laterally from the central tubular member 108 from the first end 136 connected to the central tubular member 108 to the second opening 138 including the opening 112. A lumen 144 of the laterally extending tubular member 110 is in communication with the central lumen 134 of the central tubular member lumen 136 so that blood received within the lumen 144 of the laterally extending tubular member 110 is passed into the central lumen 134. Blood received within the central lumen 134 is dispersed into the surrounding graft material via the openings 114 and/or the struts 140.

The opening 112 is configured to be connected to the external blood supply 10 which may include, for example, blood from the patient's own body from a donor site and/or a transfusion machine or bag. The external blood supply 10 may be connected to the opening 112 via a catheter 12 or other flexible, tubular device. The opening 112 may include a coupling element for connecting to the catheter 12 so that blood or other fluid from the external blood supply 10 flows into the graft containment device 110 via the catheter 12. The opening 112 may include coupling elements such as, for example, barbs, snap fit structures, ribbed tubes, pressure fits, valved couplings, and/or ball or pin quick-couplings for connecting to the catheter. Where the delivery structure 106 includes more than one laterally extending member 110, it may be desired to coupled multiple catheters to the graft containment device 100 at the same time. For example, a catheter as may be connected to both ends of the device 100. Openings 112 of each of the laterally extending tubular members 110 that are not in use may include a cap or other covering so that the blood supply does not flow out of those laterally extending tubular members 110 (e.g., not connected to an external blood supply).

According to an exemplary method using the graft containment device 100, graft material may be packed into the channel 104 of the body 102 with the graft material is packed against the delivery structure 106. Where the delivery structure 106 is not integrally formed with the body 102, the delivery structure 106 may be assembled with the body 102 prior to packing the body 102 with graft material. The graft material may be packed against the delivery structure 106 of the graft containment device 100 in any of a number of ways. In one embodiment, the graft material may be packed within the body 102 via a standard method using, for example, a spatula and/or a curette. In another embodiment, substitute graft material such as, for example, a Calcium Phosphate material or a hydrogel may be printed about the delivery structure 106 during 3D printing of the delivery structure 106 and/or the body 102. Cancellous bone or marrow harvested from the patient being treated may also be "printed" about the delivery structure using a 3D printing machine by depositing the harvested bone material in layers over the delivery structure 106. As described above, the delivery structure 106 may be positioned within the channel 104 so that the central tubular member 108 extends along the length of the body 102 and the second end 138 of the laterally extending tubular member 110 extends through one of the pores 124 of the body 102 to be accessible to a user of the device 100.

Once the graft containment device 100 has been packed with graft material, as desired, the graft containment device is positioned within the target space. The graft containment device 100 is then fixed to the bone, in the desired position. The graft containment device 100 may be fixed to the bone in any of a number of ways. For example, a fixation plate may be fixed to the body 102 via a plurality of bone fixation elements so that ends of the fixation plate extend beyond the first and second ends 120, 122 of the body 102 to extend over the separated portions of bone to which the graft containment device is to be fixed. The ends of the fixation plate may be fixed to the bone via bone fixation elements. As shown in FIG. 3, in another embodiment, the body 102 may include fixation tabs 150 extending from first and second ends 120, 122, the fixation tabs 150 extending over the separated portions of bone. Bone fixation elements may be inserted through openings 152 of the fixation tabs 150 to fix the graft containment device 100 to the bone.

Upon fixing the graft containment device 100 to the bone, the external blood supply 10 may be connected to the graft containment device 100 via a catheter or other flexible tube which may extend from the external blood supply to the graft containment device. An end of the catheter 12 may be coupled to the opening 112 at the second end 138 of the at least one laterally extending member 110 so that blood flows from the external blood supply, through the catheter and into the at least one laterally extending tubular member 110 connected thereto. Blood received within the laterally extending tubular member 110 is passed into the central tubular lumen 108 and dispersed into the surrounding graft material via the openings 114 and/or struts 140. Blood (or other fluid) may be dispersed into the graft material, as needed, to facilitate bone growth, healing, etc.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A bone graft containment device, comprising:
a body extending longitudinally from a first end to a second end and including a channel extending longitudinally therethrough; and
a fluid delivery structure received within the channel, the fluid delivery structure including a central tubular member extending along a length of the channel and a laterally extending tubular member extending laterally from the central tubular member to a fluid receiving opening, the central tubular member including a plurality of openings extending laterally through a wall thereof, so that, when the fluid receiving opening is connected to an external fluid source, fluid is passed through the laterally extending tubular member and the central tubular member to be dispersed via the plurality of openings to graft material packed within the channel, a first one of the openings being connected to a first strut extending radially away from the central tubular member, the first strut including a first lumen extending therethrough in communication with the first opening.

2. The device of claim 1, wherein the body is formed of a mesh material including a plurality of pores extending therethrough.

3. The device of claim 2, wherein at least one of the pores is sized and shaped to receive a portion of a bone fixation element.

4. The device of claim 2, wherein mesh material is formed of a plurality of intersecting members, the intersecting members defining the pores.

5. The device of claim 1, wherein a cross-section of the body is sized and shaped to correspond to a profile of a target bone.

6. The device of claim 1, wherein the delivery structure is integrally foi ned with the body.

7. The device of claim 1, wherein the delivery structure is configured to be positioned within the channel of the body.

8. The device of claim 1, wherein the fluid receiving opening includes a coupling element for connecting to the external fluid source.

9. The device of claim 1, wherein a second one of the openings being connected to a second strut extending radially away from the central tubular member, the second strut including a second lumen extending therethrough in communication with the second opening.

10. A system for treating a bone, comprising:
a mesh graft containment device extending longitudinally from a first end to a second end, a fluid delivery structure received within a channel of the mesh graft containment device, the fluid delivery structure including a central tubular member extending along a length of the channel and a laterally extending tubular member extending laterally from the central tubular member to a fluid receiving opening, the central tubular member including a plurality of openings extending laterally through a wall thereof; and
an external fluid source connectable to the fluid receiving opening of the laterally extending tubular member so that fluid is passed therethrough to the central tubular member to be dispersed via the plurality of openings of the central tubular member to a graft material packed within the channel a first one of the openings being connected to a first strut extending radially away from the central tubular member, the first strut including a first lumen extending therethrough in communication with the first opening.

11. The system of claim 10, wherein pores of the mesh graft containment device are sized and shaped to receive a portion of a bone fixation element therein.

12. The system of claim 11, wherein the mesh graft containment device is formed of a plurality of intersecting members, the intersecting members defining the pores.

13. The system of claim 10, wherein a cross-section of a body is sized and shaped to correspond to a profile of a target bone.

14. The system of claim 13, wherein the delivery structure is integrally formed with the body.

15. The system of claim 10, further comprising a catheter connecting the external fluid source to the laterally extending tubular member.

16. The system of claim 15, wherein the catheter is connected to the fluid receiving opening via a coupling element including one of a barb, a snap fit, a ribbed tube, a pressure fit, a valved coupling, a ball quick coupling and a pin lock quick coupling.

* * * * *